US008217126B2

(12) United States Patent
Hung et al.

(10) Patent No.: US 8,217,126 B2
(45) Date of Patent: Jul. 10, 2012

(54) FLUOROOLEFIN MONOMERS AND COPOLYMERS THEREOF

(75) Inventors: Ming-Hong Hung, Wilmington, DE (US); Sheng Peng, Hockessin, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 292 days.

(21) Appl. No.: 12/250,758

(22) Filed: Oct. 14, 2008

(65) Prior Publication Data

US 2009/0124774 A1   May 14, 2009

Related U.S. Application Data

(60) Provisional application No. 61/002,589, filed on Nov. 9, 2007.

(51) Int. Cl.
*C08F 16/24* (2006.01)
*C07C 43/00* (2006.01)
(52) U.S. Cl. ........ 526/247; 526/249; 526/250; 526/254; 526/255; 568/615; 568/683; 568/687
(58) Field of Classification Search .................. 526/247; 568/615, 683, 687
See application file for complete search history.

(56) References Cited

U.S. PATENT DOCUMENTS

| 3,577,465 | A | * | 5/1971 | Anello et al. ............... 568/685 |
| 4,522,995 | A | * | 6/1985 | Anderson et al. ........... 526/243 |
| 4,987,267 | A | * | 1/1991 | Takaoka et al. ............. 568/615 |
| 5,214,115 | A | * | 5/1993 | Langstein et al. ........... 526/247 |
| 5,481,028 | A | | 1/1996 | Petrov et al. |
| 6,046,285 | A | * | 4/2000 | Scheckenbach ............ 525/537 |
| 2006/0281946 | A1 | | 12/2006 | Morita et al. |
| 2007/0015864 | A1 | | 1/2007 | Hintzer et al. |
| 2007/0015866 | A1 | | 1/2007 | Hintzer et al. |

FOREIGN PATENT DOCUMENTS

| EP | 0571793 A1 | 12/1993 |
| GB | 1224773 A | 3/1971 |
| WO | 9830631 A | 7/1998 |
| WO | WO 01/46116 A1 | 6/2001 |
| WO | WO 0181464 A1 * | 11/2001 |

* cited by examiner

*Primary Examiner* — Mark Eashoo
*Assistant Examiner* — Nicole M Buie-Hatcher

(57) ABSTRACT

Disclosed herein are novel fluoroolefins of formula $Rf-O-(CF_2CF_2)_n(CH_2CF_2)_m-CH=CH_2$, wherein n is 1 or 2, m is 0 or 1 and Rf is a $C_1$-$C_8$ fluoroalkyl or fluoroalkoxy group. The fluoroolefins may be oxidized to manufacture fluorinated carboxylic acids. Also disclosed are fluoropolymers comprising copolymerized units of the fluoroolefins of the invention and at least one other fluoromonomer.

4 Claims, No Drawings

FLUOROOLEFIN MONOMERS AND COPOLYMERS THEREOF

CROSS-REFERENCE TO RELATED APPLICATIONS

This application claims the benefit of U.S. Provisional Application No. 61/002,589 filed Nov. 9, 2007.

FIELD OF THE INVENTION

This invention relates to certain fluoroolefin monomers and to copolymers thereof, more particularly to fluoroolefin monomers of the formula Rf—O—$(CF_2CF_2)_n(CH_2CF_2)_m$—CH=$CH_2$ wherein n is 1 or 2, m is 0 or 1 and Rf is a $C_1$-$C_8$ fluoroalkyl or fluoroalkoxy group, to copolymers thereof and to fluorinated carboxylic acids made from such monomers.

BACKGROUND OF THE INVENTION

Elastomeric fluoropolymers (i.e. fluoroelastomers) exhibit excellent resistance to the effects of heat, weather, oil, solvents and chemicals. Such materials are commercially available and are most commonly copolymers of vinylidene fluoride ($VF_2$) with hexafluoropropylene (HFP) and, optionally, tetrafluoroethylene (TFE). Other known fluoroelastomers include copolymers of TFE with a perfluoro(alkyl vinyl ether) such as perfluoro(methyl vinyl ether) (PMVE), copolymers of TFE with propylene (P) and, optionally $VF_2$, and copolymers of ethylene (E) with TFE and PMVE. Often, these fluoroelastomers also contain copolymerized units of a cure site monomer to facilitate vulcanization. While these copolymers have many desirable properties, including low compression set and excellent processability, their low temperature flexibility is not adequate for some end use applications. One particularly desirable improvement would be a reduction in glass transition temperature ($T_g$) with an accompanying extension of service temperature to lower temperatures. $T_g$ is often used as an indicator of low temperature flexibility because polymers having low glass transition temperatures maintain elastomeric properties at low temperatures.

Semi-crystalline and crystalline thermoplastic fluoropolymers (i.e. fluoroplastics) include homopolymers (e.g. polytetrafluoroethylene or polyvinylidene fluoride) or copolymers of TFE or $VF_2$ containing up to 20 wt. % of a second (different) fluoromonomer, a hydrocarbon olefin or a combination of the latter. Such copolymers include, but are not limited to THV, FEP and PFA. While these polymers have many desirable properties, in some applications, improved green strength would be beneficial.

SUMMARY OF THE INVENTION

It has been surprisingly discovered that the glass transition temperature of fluoroelastomers may be reduced and the green strength of fluoroplastics improved when a fluoroolefin of formula Rf—O—$(CF_2CF_2)_n(CH_2CF_2)_m$—CH=$CH_2$ is copolymerized with at least one other fluoromonomer to make the fluoroelastomer or fluoroplastic. In the latter formula n is 1 or 2, m is 0 or 1 and Rf is a $C_1$-$C_8$ fluoroalkyl or fluoroalkoxy group Accordingly, the present invention is directed to a fluoroolefin having the general formula Rf—O—$(CF_2CF_2)_n(CH_2CF_2)_m$—CH=$CH_2$, wherein n is 1 or 2, m is 0 or 1 and Rf is selected from the group consisting of a $C_1$-$C_8$ fluoroalkyl group and a $C_1$-$C_8$ fluoroalkoxy group.

Another aspect of the invention is a process for the preparation of a fluoroolefin comprising:

A) reacting a fluorovinyl ether of formula Rf—O—CF=$CF_2$, wherein Rf is selected from the group consisting of a $C_1$-$C_8$ fluoroalkyl group and a $C_1$-$C_8$ fluoroalkoxy group, with i) iodine monochloride, ii) HF and iii) a Lewis acid catalyst at a temperature of 50°-100° C. for 10 to 48 hours to form a fluoroalkyl iodide of formula Rf—O—$CF_2CF_2$—I wherein Rf is as defined above;

B) reacting said fluoroalkyl iodide with an olefin selected from the group consisting of tetrafluoroethylene and vinylidene fluoride to generate a compound of formula Rf—O—$(CF_2CF_2)_n(CH_2CF_2)_m$—I wherein n is 1 or 2, m is 0 or 1 and Rf is as defined above;

C) reacting said compound of formula Rf—O—$(CF_2CF_2)_n(CH_2CF_2)_m$—I with ethylene to produce a compound of formula Rf—O—$(CF_2CF_2)_n(CH_2CF_2)_m$—$CH_2CH_2$I wherein Rf, n and m are as defined above; and D) reacting said compound of formula Rf—O—$(CF_2CF_2)_n(CH_2CF_2)_m$—$CH_2CH_2$I with base to produce a fluoroolefin of formula Rf—O—$(CF_2CF_2)_n(CH_2CF_2)_m$—CH=$CH_2$, wherein Rf, n and m are as defined above.

Another aspect of the invention is a fluoropolymer comprising copolymerized units of:

A) a fluoroolefin having the general formula Rf—O—$(CF_2CF_2)_n(CH_2CF_2)_m$—CH=$CH_2$, wherein n is 1 or 2, m is 0; or 1 and Rf is selected from the group consisting of a $C_1$-$C_8$ fluoroalkyl group and a $C_1$-$C_8$ fluoroalkoxy group; and B) at least one fluoromonomer different from said fluoroolefin.

Another aspect of the invention is a process for the manufacture of a fluorinated carboxylic acid of the formula Rf—O—$(CF_2CF_2)_n(CH_2CF_2)_m$—COOH, wherein n is 1 or 2, m is 0 or 1 and Rf is selected from the group consisting of a $C_1$-$C_8$ fluoroalkyl group and a $C_1$-$C_8$ fluoroalkoxy group, said process comprising:

A) reacting a fluorovinyl ether of formula Rf—O—CF=$CF_2$, wherein Rf is selected from the group consisting of a $C_1$-$C_8$ fluoroalkyl group and a $C_1$-$C_8$ fluoroalkoxy group, with iodine monochloride, HF and a Lewis acid catalyst at a temperature of 50°-100° C. for 10 to 48 hours to form a fluoroalkyl iodide of formula Rf—O—$CF_2CF_2$—I wherein Rf is as defined above;

B) reacting said fluoroalkyl iodide with an olefin selected from the group consisting of tetrafluoroethylene and vinylidene fluoride to generate a compound of formula Rf—O—$(CF_2CF_2)_n(CH_2CF_2)_m$—I wherein n is 1 or 2, m is 0 or 1 and Rf is as defined above;

C) reacting said compound of formula Rf—O—$(CF_2CF_2)_n(CH_2CF_2)_m$—I with ethylene to produce a compound of formula Rf—O—$(CF_2CF_2)_n(CH_2CF_2)_m$—$CH_2CH_2$I wherein Rf, n and m are as defined above;

D) reacting said compound of formula Rf—O—$(CF_2CF_2)_n(CH_2CF_2)_m$—$CH_2CH_2$I with base to produce a fluoroolefin of formula Rf—O—$(CF_2CF_2)_n(CH_2CF_2)_m$—CH=$CH_2$, wherein Rf, n and m are as defined above and E) oxidizing said fluoroolefin to a fluorinated carboxylic acid having the formula Rf—O—$(CF_2CF_2)_n(CH_2CF_2)_m$—COOH, wherein n is 1 or 2, m is 0 or 1 and Rf is selected from the group consisting of a $C_1$-$C_8$ fluoroalkyl group and a $C_1$-$C_8$ fluoroalkoxy group.

DETAILED DESCRIPTION OF THE INVENTION

The novel fluoroolefins of this invention have the general formula Rf—O—$(CF_2CF_2)_n(CH_2CF_2)_m$—CH=$CH_2$, wherein n is 1 or 2, m is 0 or 1 and Rf is selected from the group consisting of a $C_1$-$C_8$ fluoroalkyl group and a $C_1$-$C_8$ fluoroalkoxy group. Specific examples of said fluoroolefins include, but are not limited to $CF_3$—O—$CF_2CF_2$—CH=$CH_2$, $C_2F_5$—O—$CF_2CF_2$—CH=$CH_2$, $C_3F_7$—O—$CF_2CF_2$—CH=$CH_2$, $C_3F_7O$—[$CF(CF_3)CF_2O]_p$—$CF_2CF_2$—CH=$CH_2$, $CF_3$—O—$CF_2CF_2CF_2CF_2$—CH=$CH_2$, $CF_3$—O—$CF_2CF_2$—$CH_2CF_2$—CH=$CH_2$, $C_2F_5$—O—$CF_2CF_2$—$CH_2CF_2$—CH=$CH_2$, $C_3F_7$—O—$CF_2CF_2$—$CH_2CF_2$—CH=$CH_2$, and $C_3F_7O$—[$CF(CF_3)CF_2O]_p$—$CF_2CF_2$—$CH_2CF_2$—CH=$CH_2$ wherein p is an integer 1 to 3.

These fluoroolefins are preferably made from fluorovinyl ethers by the following sequence of reactions. First, a fluorovinyl ether of formula Rf—O—CF=$CF_2$, wherein Rf is selected from the group consisting of a $C_1$-$C_8$ fluoroalkyl group and a $C_1$-$C_8$ fluoroalkoxy group, is reacted with i) iodine monochloride, ii) HF and iii) a Lewis acid catalyst to form a fluoroalkyl iodide of formula Rf—O—$CF_2CF_2$—I wherein Rf is as defined above. Examples of Lewis acid catalysts that may be employed in the process include, but are not limited to $BF_3$, $SbF_3$, $TaF_5$, $NbF_5$, $SbCl_5$ and $TiCl_4$. The reaction typically takes place at a temperature between 50° and 100° C. for 10 to 48 hours. The resulting fluoroalkyl iodide is then reacted with tetrafluoroethylene or vinylidene fluoride to produce a compound of formula Rf—O—$(CF_2CF_2)_n(CH_2CF_2)_m$—I wherein n is 1 or 2, m is 0 or 1, and Rf is as defined above.

The compound of formula Rf—O—$(CF_2CF_2)_n(CH_2CF_2)_m$—I is then reacted with ethylene to produce a compound of formula Rf—O—$(CF_2CF_2)_n(CH_2CF_2)_m$—$CH_2CH_2I$ wherein Rf, n and m are as defined above. The reaction with ethylene may be run at a temperature of 190° to 230° C. for 6 to 24 hours, or if in the presence of a radical initiator such as benzoyl peroxide or a Vazo® initiator (available from DuPont), at a temperature between 60° to 90° C.

The Rf—O—$(CF_2CF_2)_n(CH_2CF_2)_m$—$CH_2CH_2I$ is then dehydrofluorinated with base to produce a fluoroolefin of the invention having the formula Rf—O—$(CF_2CF_2)_n(CH_2CF_2)_m$—CH=$CH_2$, wherein Rf, n and m are as defined above.

This fluoroolefin may be oxidized and cleaved to form a fluorinated carboxylic acid having the formula Rf—O—$(CF_2CF_2)_n(CH_2CF_2)_m$—COOH, wherein Rf, n and m are as defined above. Oxidizing agents that may be employed in this reaction include, but are not limited to $KMnO_4$ and $CrO_3$ with a strong acid such as sulfuric acid. The resulting fluorinated carboxylic acid may be reacted with base (e.g. $NH_4HCO_3$, NaOH, KOH, etc.) to form an anionic fluorosurfactant of formula Rf—O—$(CF_2CF_2)_n(CH_2CF_2)_m$—COOM, wherein M is a univalent cation such as $NH_4^+$, $Na^+$, $K^+$, etc. These fluorosurfactants may be employed as dispersing agents in the polymerization of fluoropolymers.

The fluoroolefins of the invention may also be employed to manufacture fluoropolymers. Fluoropolymers of the invention, both fluoroelastomers and fluoroplastics, comprise copolymerized units of the above described fluoroolefin and at least one other fluoromonomer, different from said fluoroolefin. Preferably the fluoropolymers comprise 0.5 to 10 mol % of the fluoroolefin of the invention.

Fluoromonomers that may be contained in the fluoropolymers of the invention include, but are not limited to tetrafluoroethylene (TFE), chlorotrifluoroethylene (CTFE), hexafluoropropylene (HFP), vinylidene fluoride ($VF_2$), vinyl fluoride (VF), a perfluoro vinyl ether, as well as functional monomers such as $CF_2$=$CFOCF_2CF(CF_3)$—O—$CF_2CF_2$—$COOCH_3$, and $CF_2$=$CFOCF_2CF(CF_3)$—O—$CF_2CF_2$—$SO_2F$.

A preferred class of perfluoro vinyl ethers that may be employed in the fluoropolymers of the invention includes ethers of the formula

$CF_2$=$CFO(CF_2CFXO)_nR_f$ where X is F or $CF_3$, n is 0-5, and $R_f$ is a perfluoroalkyl group of 1-6 carbon atoms.

A most preferred class of perfluoro vinyl ethers includes those ethers wherein n is 0 or 1 and $R_f$ contains 1-3 carbon atoms. Examples of such perfluorinated ethers include perfluoro(methyl vinyl ether) (PMVE) and perfluoro(propyl vinyl ether) (PPVE).

Other useful perfluoro vinyl ethers include those of the formula

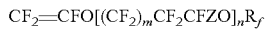
$CF_2$=$CFO[(CF_2)_mCF_2CFZO]_nR_f$ where $R_f$ is a perfluoroalkyl group having 1-6 carbon atoms, m=0 or 1, n=0-5, and Z=F or $CF_3$. Preferred members of this class are those in which $R_f$ is $CF_3$, m=1, n=1, and Z=F; and $R_f$ is $C_3F_7$, m=0, and n=1.

Additional perfluoro vinyl ethers include compounds of the formula

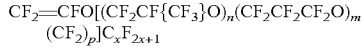
$CF_2$=$CFO[(CF_2CF\{CF_3\}O)_n(CF_2CF_2CF_2O)_m(CF_2)_p]C_xF_{2x+1}$ where m and n independently=0-10, p=0-3, and x=1-5. Preferred members of this class include compounds where n=0-1, m=0-1, and x=1.

Additional examples of useful perfluoro vinyl ethers include

$CF_2$=$CFOCF_2CF(CF_3)O(CF_2O)_mC_nF_{2n+1}$ where n=1-5, m=1-3, and where, preferably, n=1.

In addition to at least one fluoromonomer different from the fluoroolefin of this invention, the fluoropolymers of this invention may also contain copolymerized units of a hydrocarbon olefin such as ethylene or propylene.

Furthermore fluoropolymers of the invention may contain 0.1 to 7 mole percent copolymerized units of cure site monomers commonly employed in the fluoropolymer industry. Such cure site monomers include, but are not limited to bromine- and iodine-containing olefins such as bromotrifluoroethylene, iodotrifluoroethylene, 4-bromo-3,3,4,4-tetrafluorobutene, and 4-iodo-3,3,4,4-tetrafluorobutene. Such cure site monomers are well known in the art (e.g. U.S. Pat. Nos. 4,214,060; 5,214,106; and 5,717,036). Other cure site monomers include 2-hydropentafluoropropene, 1-hydropentafluoropropene; 3,3,3-trifluoropropene; and nitrile group-containing fluoroolefins or fluorovinyl ethers such as those disclosed in U.S. Pat. No. 6,211,319 B1 (e.g. perfluoro(8-cyano-5-methyl-3,6-dioxa-1-octene)).

Fluoropolymers of this invention may be prepared by known emulsion, suspension or solution polymerization processes. A chain transfer agent such as a perfluoroalkyldiiodide (e.g. I—$(CF_2)_4$—I), alcohols, ketones or hydrocarbons may be employed to control the polymerization.

Fluoroelastomers of the present invention are useful in production of gaskets, tubing, seals, hoses, O-rings and other molded components. Such articles are generally produced by compression molding a compounded formulation of the elastomer, a curing agent and various additives, curing the molded article, and then subjecting it to a post cure cycle. The cured elastomer parts have excellent low temperature flexibility and processability as well as excellent thermal stability and chemical resistance. They are particularly useful in applications such as seals and gaskets requiring a good combination of oil resistance, fuel resistance and low temperature flexibility, for example in fuel injection systems, fuel line connector systems and in other seals for high and low temperature automotive uses.

Fluoroplastics of the present invention are useful in production of seals, wire and cable jacketing, hoses, etc. They are particularly useful in applications requiring good green strength such as parts for sealing, molding and injection applications.

The invention is now illustrated by certain embodiments wherein all parts and percentages are by weight unless otherwise specified.

EXAMPLES

Test Methods

Compositions and microstructures were determined by $^{19}$F and $^1$H NMR. The NMR spectra were recorded on a Bruker AC 400 (400 MHz) instrument, using deuterated acetone as solvent and tetramethylsilane (TMS) (or $CFCl_3$) as the references for $^1$H (or $^{19}$F) nuclei. Coupling constants and chemical shifts are given in Hz and ppm, respectively. The experimental conditions for $^1$H (or $^{19}$F) NMR spectra were the following: flip angle 90° (or 30°), acquisition time 4.5 s (or 0.7 s), pulse delay 2 s (or 5 s), number of scans 16 (or 64), and a pulse width of 5 μs for $^{19}$F NMR.

Example 1

In a 1300 mL stainless steel shaker tube was charged perfluoro(propyl vinyl ether) (PPVE, 346 grams, 1.30 moles), iodine monochloride (248.5 grams, 1.53 moles), HF (500 grams, 25 moles), and boron trifluoride (50 grams, 0.737 moles). The tube was sealed and cool-evacuated. By "cool-evacuated" is meant that oxygen was removed from the reactor by cooling reactor contents sufficiently so that all ingredients remained in the reactor while a vacuum was applied to remove oxygen. The tube and contents were then heated at 75° C. for 24 hours while being shaken. After cooling, the product mixture was unloaded from the tube, and washed with saturated sodium bisulfite solution to remove unreacted residual iodine. After drying, the product ($CF_3CF_2CF_2$—O—$CF_2CF_2$—I) was distilled to a clear colorless liquid, bp. 85-86° C., yield: 400 grams (75%).

In a 1300 mL stainless steel shaker tube was charged 1-iodo-3-oxa-perfluorohexane ($CF_3CF_2CF_2$—O—$CF_2CF_2$—I) (370.8 grams, 0.90 moles) and d-(+)-Limonene (1.0 gram). The tube was sealed and cool-evacuated, and ethylene (42 grams, 1.50 moles) was transferred into the tube. The tube was sealed again and was heated at 220° C. for 10 hours. The product ($CF_3CF_2CF_2$—O—$CF_2CF_2$—$CH_2CH_2$—I) was unloaded from the tube and purified by distillation to give a pale-pink clear liquid, bp. 65-69° C. at 50 mm Hg. Yield: 340 grams (86%). $^1$H-NMR ($CDCl_3$, 400 MHz): δ 3.24 (t, J=8.7 Hz, 2H), 2.72 (m, 2H); $^{19}$F-NMR ($CDCl_3$, 376.89 MHz): −81.8 (t, J=7.5 Hz, 3F), −84.5 (m, 2F), −88.0 (t, J=13.2 Hz, 2F), −119.3 (t, J=17 Hz, 2F), −130.4 (s, 2F).

In a reaction flask was charged TLF-2370C phase transfer catalyst ($[C_{12}H_{25}][PhCH_2][CH_2CH(OH)CH_3]_2$ available from DuPont) (60% aqueous solution) (29.6 grams, 0.042 moles), 10 M KOH solution (280 mL, 2.80 moles), along with 1-iodo-1,1,2,2-tetrahydro-5-oxa-perfluorooctane ($CF_3CF_2CF_2$—O—$CF_2CF_2$—$CH_2CH_2$—I) (176 grams, 0.40 moles). The reaction mixture was allowed to stir for 14 hours at ambient temperature. The product mixture was transferred into a separatory funnel and the bottom organic layer was separated, washed with water twice, dried over magnesium sulfate, then distilled to give $CF_3CF_2CF_2$—O—$CF_2CF_2$—CH=$CH_2$ product as a clear, colorless liquid, bp. 75-76° C., Yield: 172 grams (72%). $^1$H-NMR ($CDCl_3$, 400 MHz): δ 5.90 (m, 1H), 5.92 (m, 2H); $^{19}$F-NMR ($CDCl_3$, 376.89 MHz): −81.9 (t, J=7.5 Hz, 3F), −85.1 (m, 2F), −85.3 (t, J=13.2 Hz, 2F), −118.3 (d, J=11.3 Hz, 2F), −130.5 (s, 2F).

Example 2

In a 400 mL stainless steel shaker tube was charged de-ionized water (280 mL), ammonium perfluorooctanoate surfactant (1.5 grams), disodium phosphate heptahydrate (1.0 gram), ammonium persulfate (0.1 gram) and 1,1,2-trihydro-5-oxa-perfluoro-1-octene monomer ($CF_3CF_2CF_2$—O—$CF_2CF_2$—CH=$CH_2$) (4 grams). The tube was sealed and cool-evacuated. Tetrafluoroethylene (TFE, 45 grams, 0.45 moles) and perfluoro(methyl vinyl ether) (PMVE, 38 grams, 0.229 moles) were transferred into the tube. The tube was sealed again and was then heated at 75° C. for 8 hours. After cooling, the latex was unloaded from the tube and coagulated with saturated magnesium sulfate solution. The precipitated polymer was collected, and washed thoroughly with warm water. After drying, a white polymer (69 grams) was obtained. This polymer had a Tg of −6.14° C. as measured by DSC, and had a composition of TFE/PMVE/$CF_3CF_2CF_2$—O—$CF_2CF_2$—CH=$CH_2$=60.0/37.9/2.1 (mole %) as determined by NMR spectroscopy.

Example 3

In a semi-batch reactor was charged de-ionized water (2,000 mL), ammonium perfluorooctanoate surfactant (3.9 grams), disodium phosphate heptahydrate (20 gram), and 1,1,2-trihydro-5-oxa-perfluoro-1-octene monomer ($CF_3CF_2CF_2$—O—$CF_2CF_2$—CH=$CH_2$) (20 grams). The reactor was cool-evacuated, and was then charged with a gas mixture of vinylidene fluoride ($VF_2$) (320 grams), TFE (10 grams), and PMVE (670 grams) until the pressure reached 1.38 MPa at 80° C. Ammonium persulfate (20 mL of a 2 wt % aqueous solution) was fed initially, followed by feeding the 2 wt. % solution at a rate of 10 mL/min. When a pressure drop of 13.8 kPa was observed, a gas mixture of $VF_2$ (212 grams/hr), TFE (37 grams/hr), and PMVE (140 grams/hr) was fed at a rate sufficient to maintain the reactor pressure at 1.24 MPa. The polymerization was stopped when about a total amount of 720 grams of gas had been fed. The polymer latex was unloaded from the reactor and was coagulated and isolated as described in the above example. The white polymer obtained (760 grams) was analyzed to have a composition of $VF_2$/TFE/PMVE/$CF_3CF_2CF_2$—O—$CF_2CF_2$—CH=$CH_2$ of 75.0/6.4/18.6/0.05 (mole %) as determined by NMR spectroscopy. The Tg of this polymer was −30.1° C. as determined by DSC.

Example 4

$KMnO_4$ (50 g, 0.315 mol) was dissolved in deionized water, followed by addition of $H_2SO_4$ (53 g, 0.541 moles). $C_3F_7OCF_2CF_2CH$=$CH_2$ (prepared as in the examples above) (20 g, 0.094 moles) was added dropwise at 60° C. to the permanganate solution, and the oxidation reaction was run at 70° C. for 3 hours. Then, the resulting solution was cooled to room temperature and thrice extracted with 100 mL ether. The extract was dried over $MgSO_4$ and then filtered. The fluorinated carboxylic acid product ($C_3F_7OCF_2CF_2COOH$) was distilled via vacuum distillation (9 g, 29% yield), b.p. 62-63° C. at 30 mm Hg.
$^{19}$F NMR (376 MHz, $CDCl_3$): −84.52 (3F, t, J=8 Hz), −84.7~−85.0 (2F, m), −86.17~86.23 (2F, m), −125.20~−125.21 (2H, t, J=2.1 Hz), −134.49 (2F, s).

Ammonium bicarbonate solution (1.48 g, 0.0187 mol, in 10 mL water) was added to the fluorinated carboxylic acid $C_3F_7OCF_2CF_2COOH$ (6 g, 0.0182 mol) produced above. The reaction was stirred at room temperature for an hour. Water was removed in a rotovap resulting in the product ($C_3F_7OCF_2CF_2COONH_4$) as a white solid (4 g, 79% yield), b.p. 121-123° C.

$^{19}$F NMR (376 MHz, $CDCl_3$): −81.61 (3F, t, J=8 Hz), −84.7~−85.0 (2F, m), −86.17~86.23 (2F, m), −121.17~121.19 (2H, t, J=2.1 Hz), −130.27 (2F, s).

What is claimed is:

1. A fluoroolefin selected from the group consisting of $CF_3$—O—$CF_2CF_2$—CH=$CH_2$, $CF_3$—O—$CF_2CF_2CF_2CF_2$—CH=$CH_2$, $CF_3$—O—$CF_2CF_2$—$CH_2CF_2$—CH=$CH_2$, and $C_2F_5$—O—$CF_2CF_2$—$CH_2CF_2$—CH=$CH_2$.

2. A fluoropolymer comprising copolymerized units of:
   A) a fluoroolefin selected from the group consisting of $CF_3$—O—$CF_2CF_2$—CH=$CH_2$, $CF_3$—O—$CF_2CF_2CF_2CF_2$—CH=$CH_2$, $CF_3$—O—$CF_2CF_2$—$CH_2CF_2$—CH=$CH_2$, and $C_2F_5$—O—$CF_2CF_2$—$CH_2CF_2$—CH=$CH_2$; and
   B) at least one fluoromonomer different from said fluoroolefin.

3. A fluoropolymer of claim 2 wherein fluoromonomer is selected from the group consisting of tetrafluoroethylene, chlorotrifluoroethylene, hexafluoropropylene, vinylidene fluoride, vinyl fluoride and a perfluoro vinyl ether.

4. A fluoropolymer of claim 2 further comprising 0.1 to 7 mole percent copolymerized units of cure site monomer.

* * * * *